(12) United States Patent
McAfee

(10) Patent No.: US 8,062,335 B1
(45) Date of Patent: Nov. 22, 2011

(54) PLATE SYSTEMS AND METHODS OF USE

(75) Inventor: Paul McAfee, Sparks, MD (US)

(73) Assignee: Globus Medical, Inc., Audubon, PA (US)

( * ) Notice: Subject to any disclaimer, the term of this patent is extended or adjusted under 35 U.S.C. 154(b) by 323 days.

(21) Appl. No.: 11/758,595

(22) Filed: Jun. 5, 2007

Related U.S. Application Data

(60) Provisional application No. 60/810,694, filed on Jun. 5, 2006.

(51) Int. Cl.
*A61B 17/70* (2006.01)
(52) U.S. Cl. ........................................................ 606/246
(58) Field of Classification Search .......... 606/280–291, 606/70–71, 902–906; 623/17.11–17.16
See application file for complete search history.

(56) References Cited

U.S. PATENT DOCUMENTS

| | | | | |
|---|---|---|---|---|
| 5,674,296 A | * | 10/1997 | Bryan et al. | 623/17.16 |
| 6,228,085 B1 | * | 5/2001 | Theken et al. | 606/289 |
| 6,235,033 B1 | * | 5/2001 | Brace et al. | 606/288 |
| 6,306,170 B2 | * | 10/2001 | Ray | 623/17.11 |
| 7,220,263 B2 | * | 5/2007 | Cordaro | 606/70 |

* cited by examiner

*Primary Examiner* — Thomas C. Barrett
*Assistant Examiner* — Sameh Boles

(57) ABSTRACT

A spinal system having a plate with at least one nesting point and at least one screw hole for receiving a screw. The system also includes a keel having a first and second keel wing attached to the plate and a structure having at least one screw hole, the structure configured to be placed between two vertebrae in a spine. The first and second keel wing are configured with at least one screw hole each which correspond to the at least one screw hole of the plate and the at least one screw hole of the structure. The first and second keel wing are configured with a first and second bottom portion, and the first and second bottom portions having a first and second cup for receiving a portion of the screw and the first and second bottom portions being adapted to lock the screws from backing out.

11 Claims, 9 Drawing Sheets

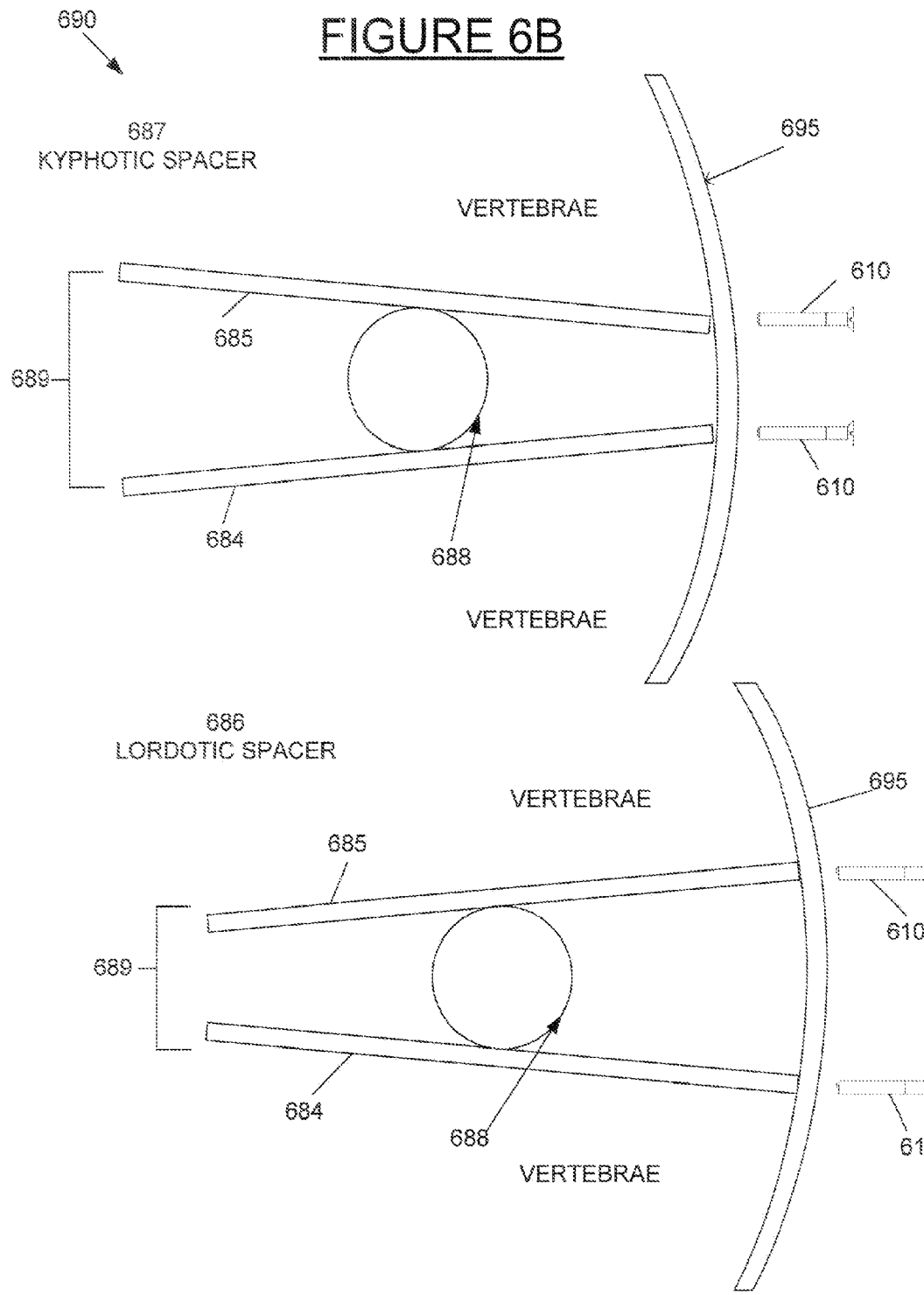

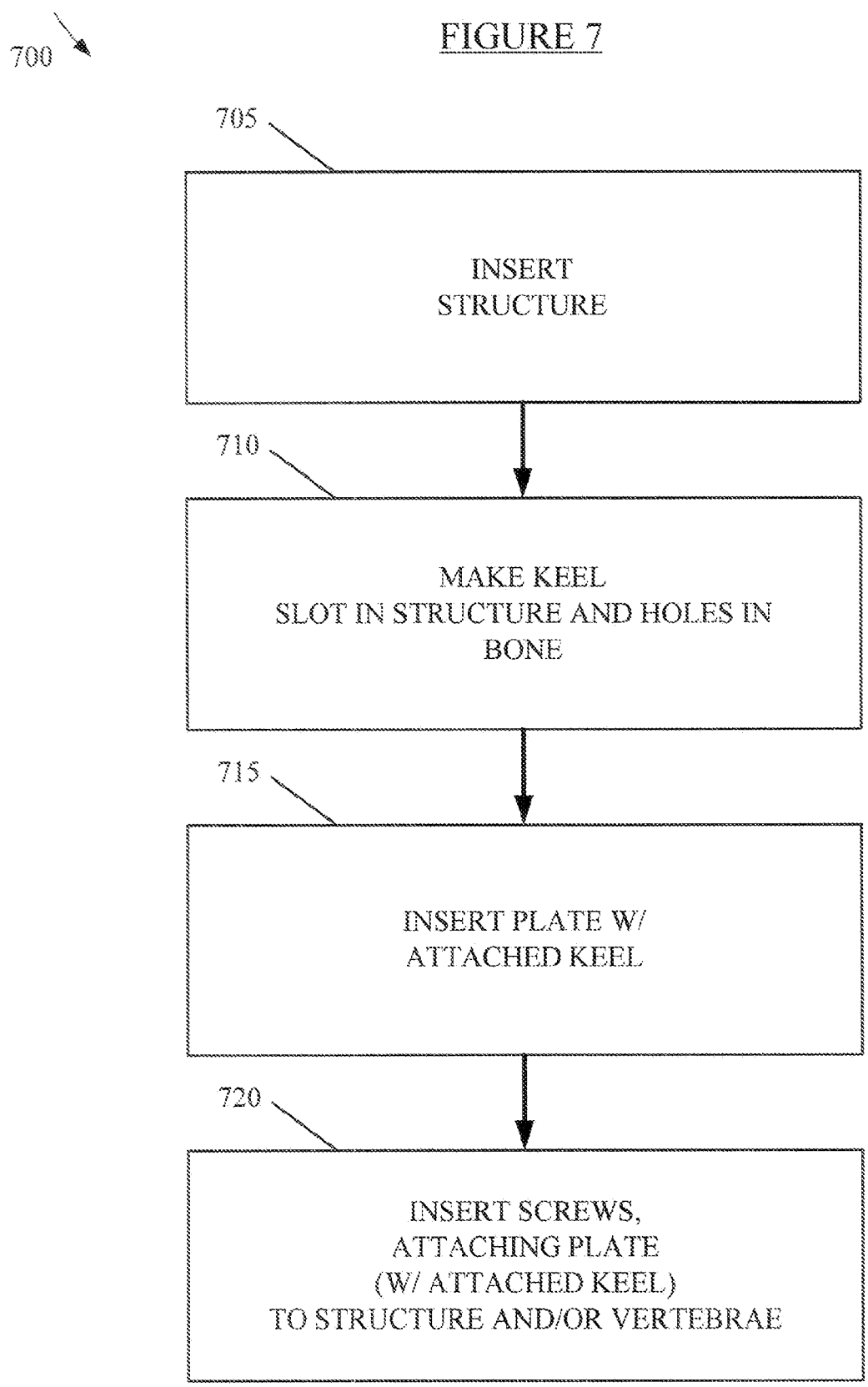

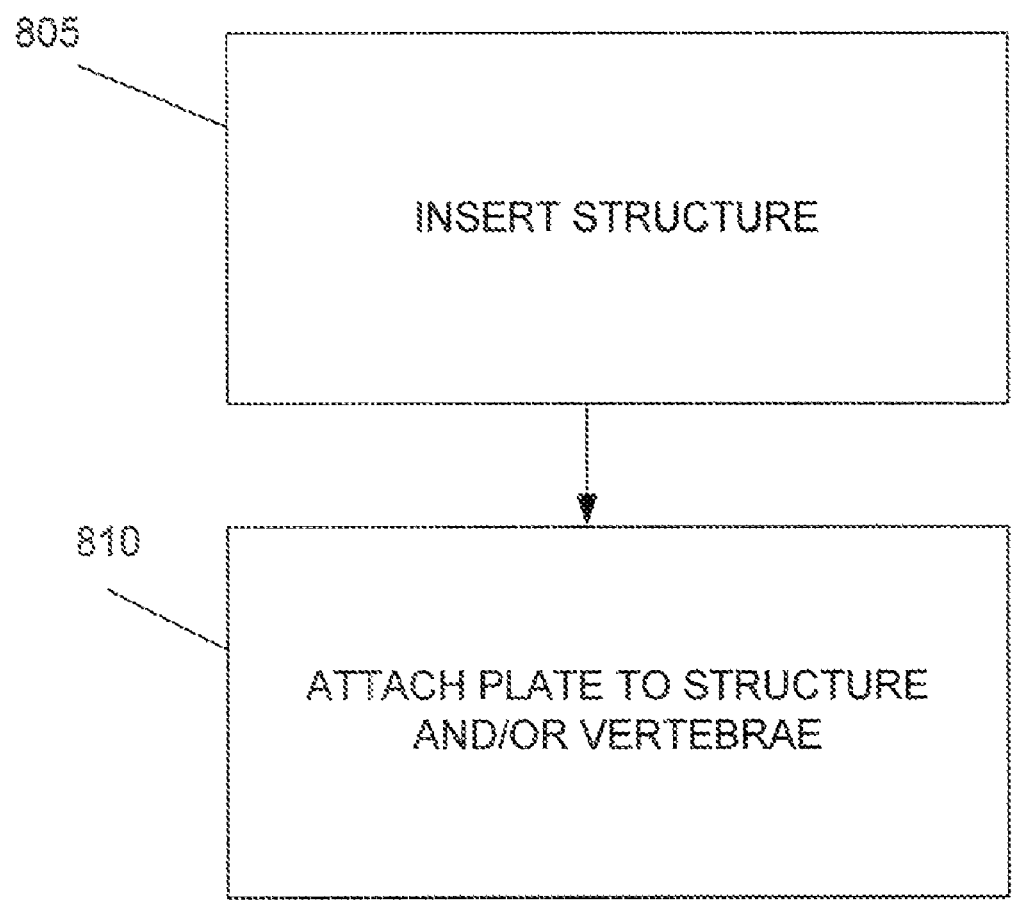

PLATE SYSTEMS AND METHODS OF USE

This application claims priority to provisional application 60/810,694, filed on Jun. 5, 2006, and entitled "Integrated Cervical Plate-Cage System", which is herein incorporated by reference.

BRIEF DESCRIPTION OF THE FIGURES

FIGS. 6A-6B illustrate views of other embodiments of plate systems, according to several embodiments of the invention.

FIGS. 7-8 illustrate methods for utilizing the plate systems, according to one embodiment of the invention.

DESCRIPTION OF EMBODIMENTS OF THE INVENTION

Figure 1:
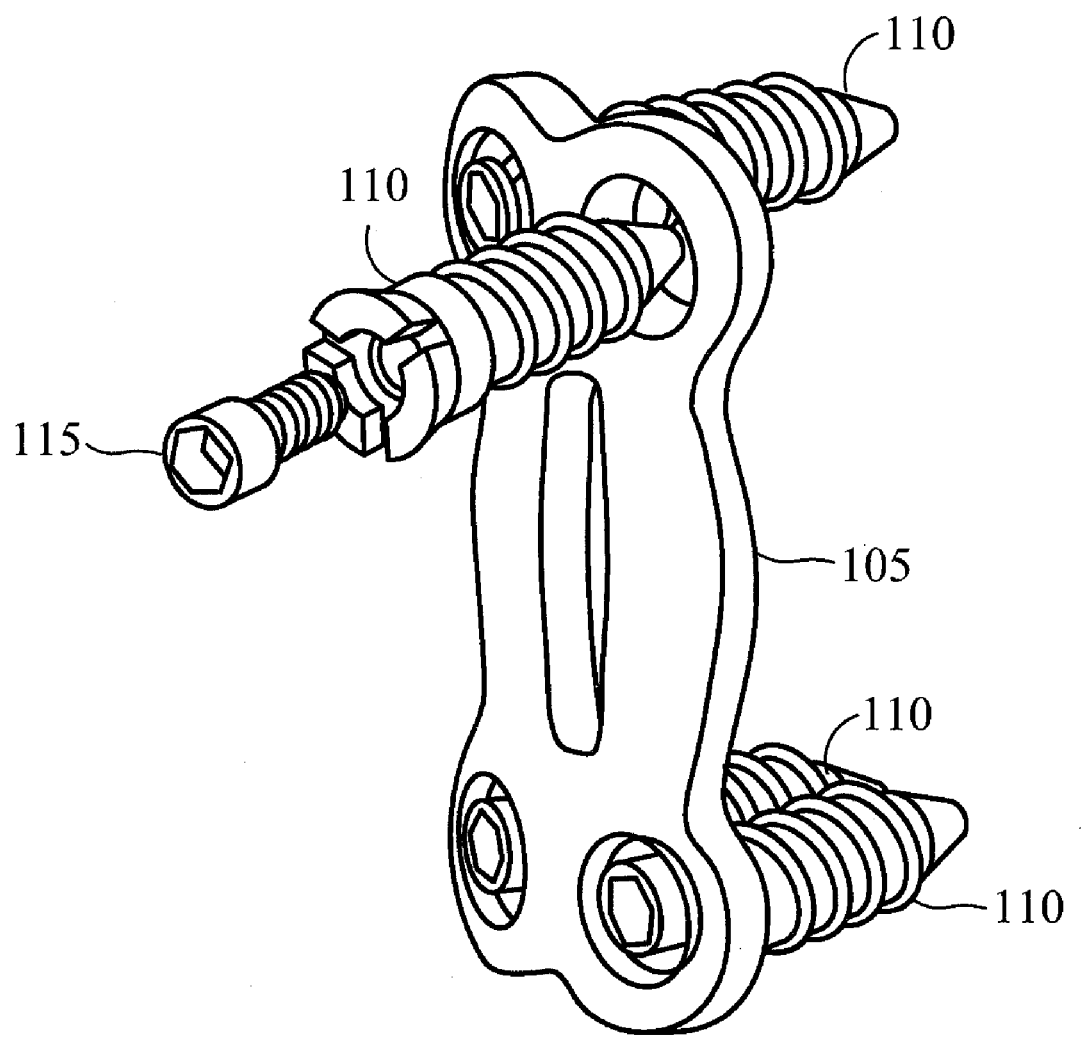
FIG. 1 illustrates a perspective view of a plate, according to one embodiment of the invention.

FIG. 1 illustrates a perspective view of a plate 105, according to one embodiment of the invention. In one embodiment, the plate 105 is utilized to hold in a structure (e.g., cage) that is placed between the vertebrae of the spine. Note that the structure can be a cage and/or spacer and/or structural allograft, and/or vertebral body replacement, and/or any combination thereof can be used. Also, note that, in one embodiment, expandable and/or movable structures can be utilized. The structure can be placed between the vertebrae of the spine for various reasons. For example, the plate system 100 can be utilized on the cervical area of the spine for a structural graft. It can also be used in other areas, such as the thoracic spine, the lumbar spine, and the lumbosacral spine. Referring to FIG. 1, the plate 105 is attached to the bone of the spine using screws 110. In one embodiment, the screws 110 can be screwed in using a reamer 115, screwdriver, or another object. In one embodiment, the reamer 115 could have a depth stop.

Figure 2:
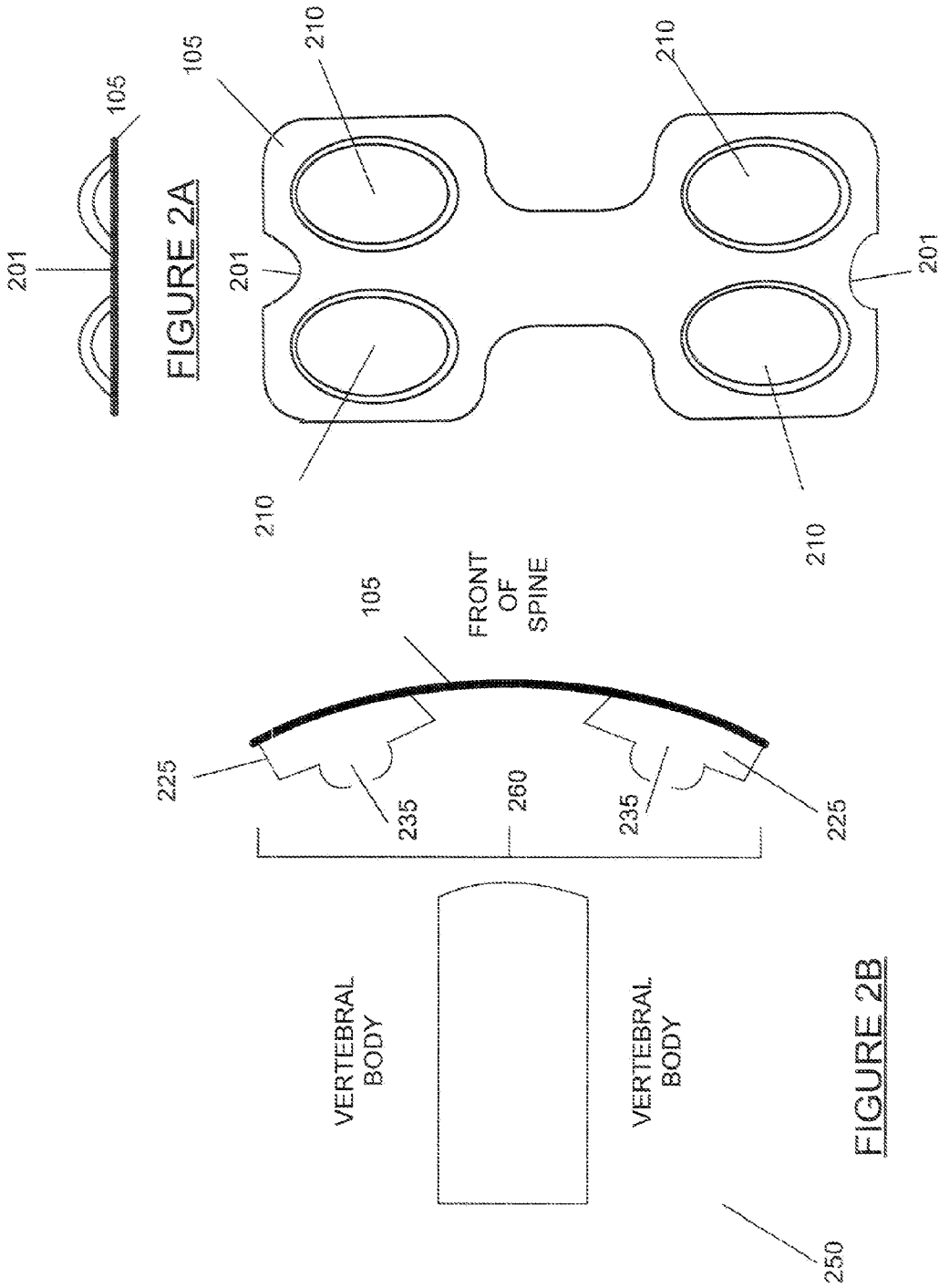
FIGS. 2A, 2B, and 2C illustrate various views of a plate system, according to one embodiment of the invention.

FIGS. 2A, 2B, and 2C illustrates various views of a plate system 100, according to one embodiment of the invention. FIG. 2A illustrates a top view of the plate 105. The plate 105 can have various holes 210, which allow the screws to be screwed into the plate 105. Note that in one embodiment, the plate 105 can be made of titanium. In one embodiment, the titanium plate can be made with 10 degrees per lordosis per level. Thus, the plate can be manufactured with a prebent curvature to it which matches the ideal shape of the spine. In addition, the plate can be of a low anterior profile, for example, less than 1 mm. In one embodiment, locking pins (e.g., Casper locking pins, or any other locking pins) are in place so that the structure can be locked in place. In one embodiment, there are cut outs 201 for the locking pins at each end of the plate 105, which can be of a shape which corresponds with the shape of the locking pins.

FIG. 2B illustrates a side view of the plate system 100. The plate system 100 comprises the plate 105, a keel 260 (comprising a two keel wings 225, and cups 235 for the screwheads of the screws 110. In one embodiment, the plate is attached to the keel 260. Note that the plate 105 and/or the keel 260 (and or the keel wings 225) can be contoured or bent in a manner that would serve to lock in the structure 250 more effectively. The keel can connect to the structure 250, which has been inserted between two vertebrae. Note that, in one embodiment, the shape of the keel 260, (including the shape of the keel wings 225) can be any shape, as a keel template is make of the keel 260, and the keel template is used to make a keel slot in the structure 260. Note that, in another embodiment, the keel 260 and/or keel wings 225 can be shaped to coincide with the shape of the structure 250. In one embodiment, the keel can be 3 or 4 mm deep. In an additional embodiment, a PEEK (polyetheretherketone) cage can be utilized as the structure 250. A PEEK cage is a spinal cage used in spinal surgery to separate two vertebrae. Holes are drilled in the vertebrae bone so that the keel 260 (and the attached plate 105) can be secured to the vertebrae bone with screws. Note that, in one embodiment, because the keel 260 interlocks with the structure 250, the plate 105 can be very low profile (intraosseous or mostly intraosseous, i.e., within the bone) and thus the plate 105 does not protrude out far beyond the spine. For example, in one embodiment, the entire plate system 100 and structure construct has a maximum anterior profile of 1 mm because the wings of the keel 260 and the screwheads of the screws 110 are intraosseous. The keel 260 can allow the plate 105 to be thinner. This makes the plate system more comfortable and safe for the patient. For example, with a cervical low profile plate, the patient may experience less hoarseness and less discomfort or pain in the throat with the use of a low profile plate versus the use of higher profile plate. It should also be noted, that, in one embodiment, the plate system 100 can be used with standard dimensions and instruments.

FIG. 2C illustrates a top view of the plate system 100. The plate 105 has nesting points 235 for the screwheads that are on the undersurface of the plate and reside within the anterior margins of the spinal column. They do not project anteriorly into the soft tissue structures of the neck.

Figure 3:
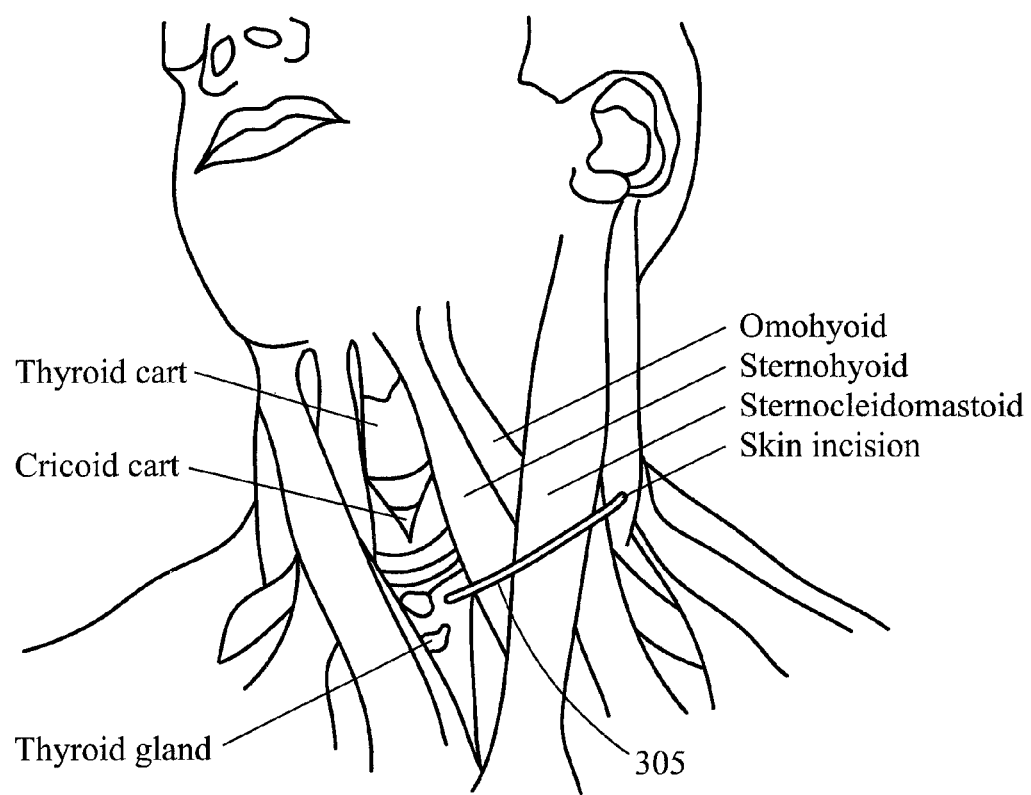
FIGS. 3-4 illustrate various views of the neck and spine, according to several embodiments of the invention.
Figure 4:
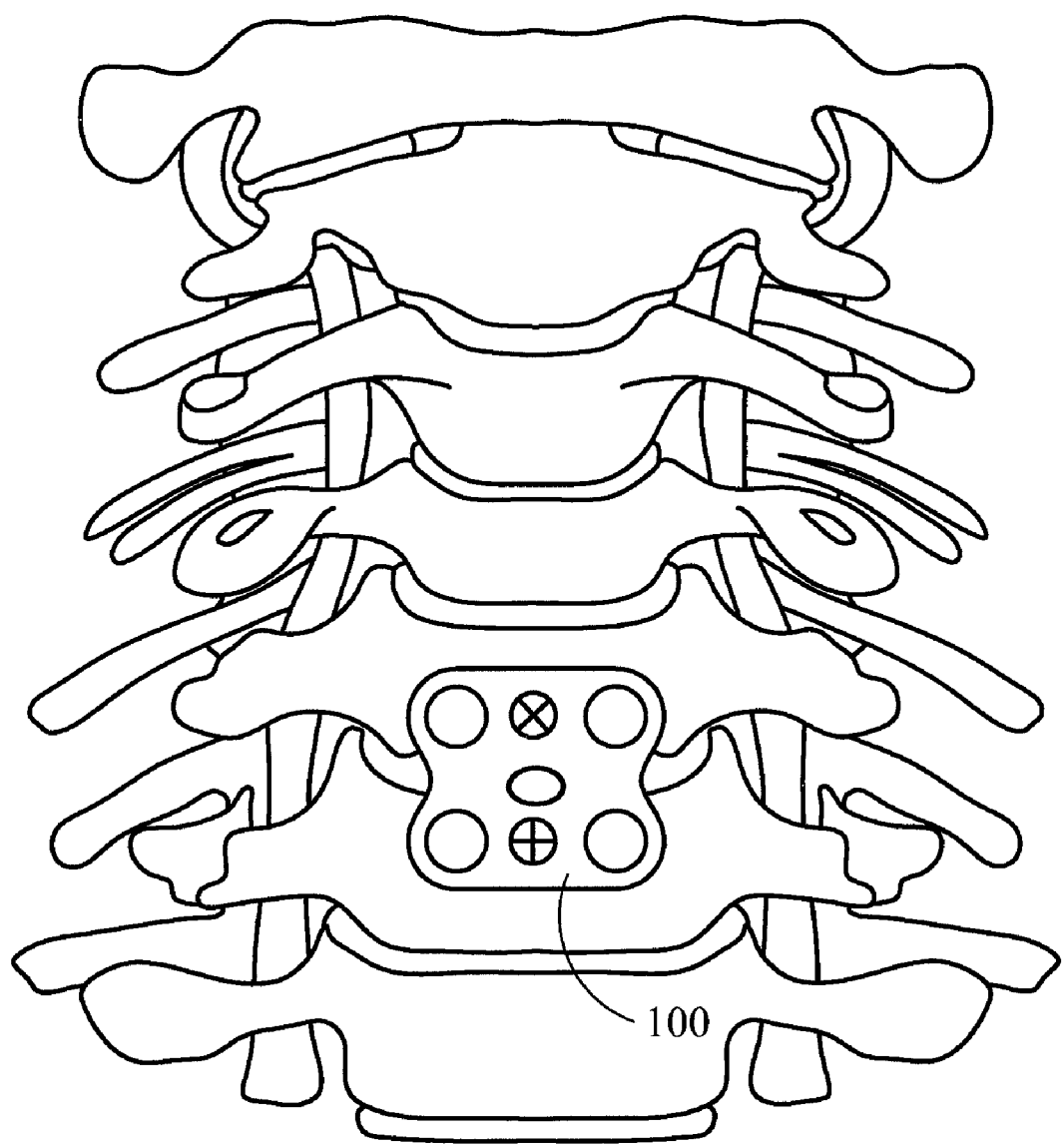

FIGS. 3-4 illustrate various views of the neck and spine, according to several embodiments of the invention. FIG. 3 illustrates an anterior approach to the neck and a possible incision 305 that could be used for placement of the cage and plate system. Note that many other incision points are possible. FIG. 4 illustrates a perspective view of the spine, with the plate system 100, according to one embodiment of the invention. In one embodiment, the plate system 100 is very flat and does not protrude much (e.g., 1 mm or less) because the keel and the screwdrivers are mostly inset in the bone (i.e., intraosseous).

Figure 5A:
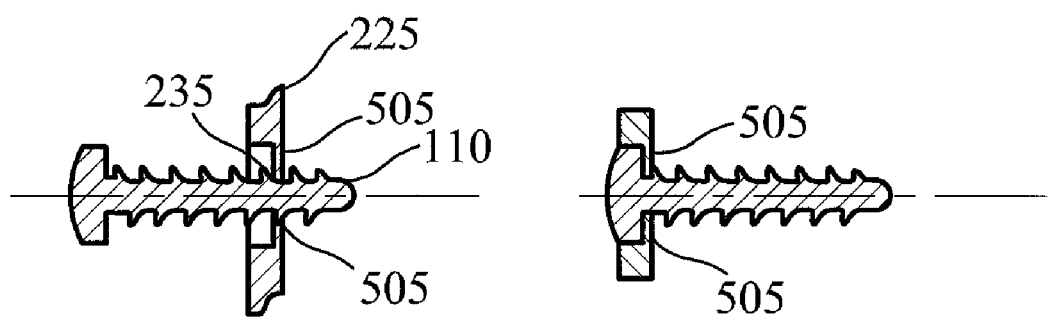
FIGS. 5A-5B illustrate various views of the screwdrivers and the keel, according to several embodiments of the invention.
Figure 5B:
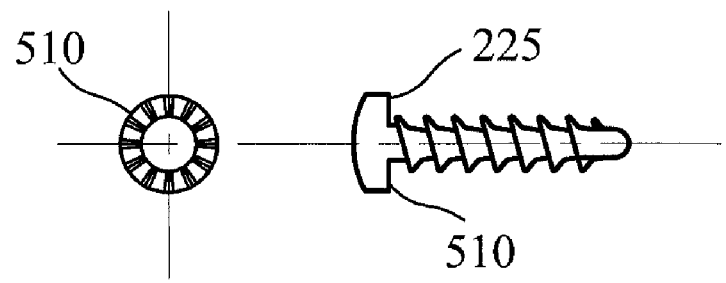

FIGS. 5A-5B illustrate various views of the screwdrivers 110 and the keel wing 225, according to several embodiments of the invention. In one embodiment, as illustrated in FIG. 5A, the keel wing 225 can have a bottom portion 505 underneath part of the cup 235 for the screw, which bottom portion 505 can be used to lock in the screws so they are not easily unscrewed. Thus, the last screw thread can slip through the bottom portion 505, but it will not be able to easily find the same opening to back out. In an additional embodiment, as illustrated in FIG. 5B, the underneath portion 510 of the head of the screw can be ribbed or made rough so that it connects more securely with the keel wing 225.

Figure 6A:
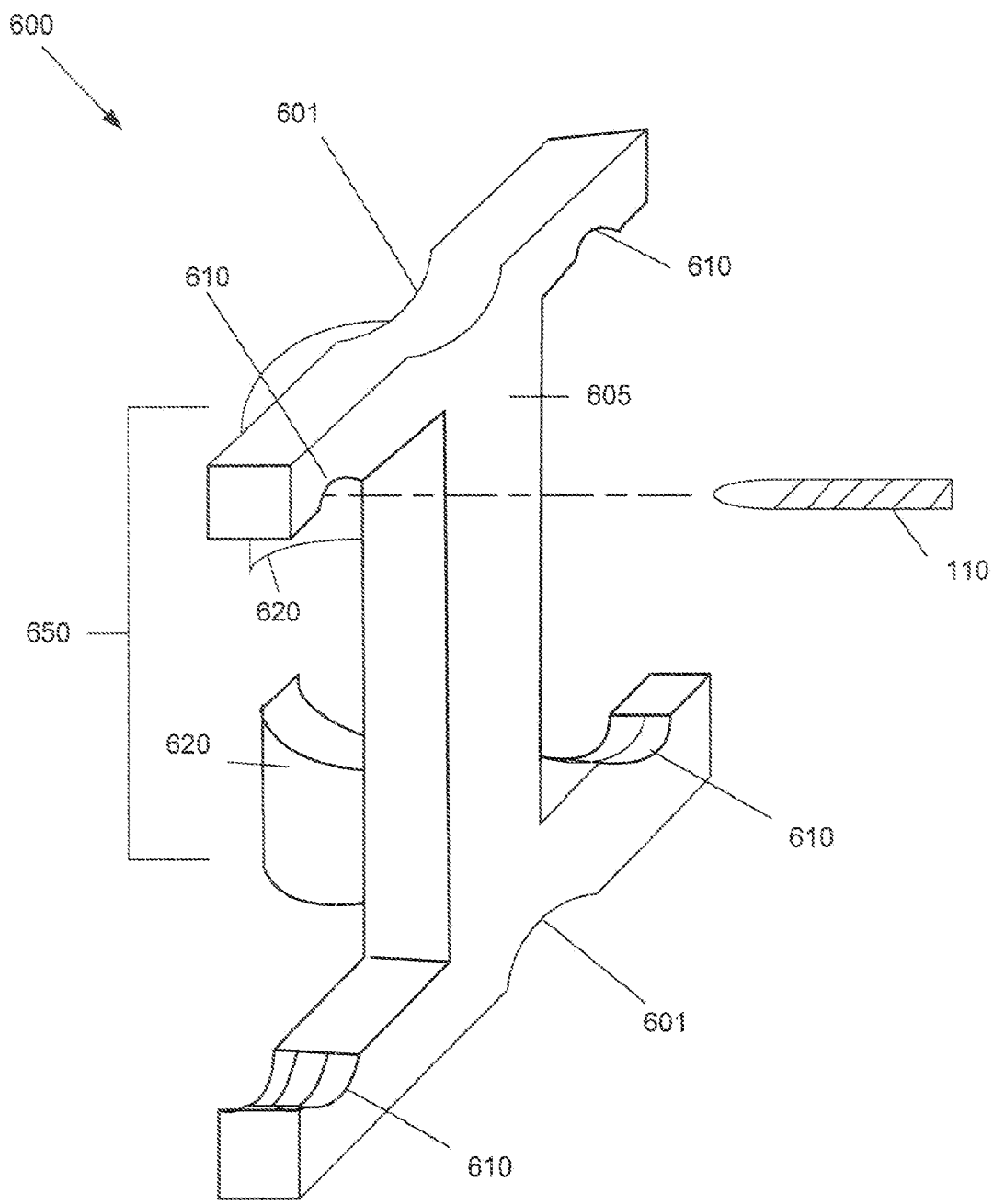

FIG. 6A is a perspective view of another embodiment of a plate system 600, according to one embodiment of the invention. The plate system 600 has a plate 605, a keel 650 (comprising a keel wings 620), and screw cavities 610. Note that in this embodiment, the plate 605 is in the form of an I-beam. The I-beam embodiment can serve as a tension band in cervical extension and can prevent rotation and extrusion out of the structure. The screw cavities 610 are not full circles, but rather semicircles with grooves, because the screws will be secured with the screw cavities 610, as well as the holes that have been drilled in the bone. The screws then can be inserted into the screw cavities 610 and the holes in the bone in order to secure the plate 605 (with the attached keel 650) to the vertebrae bone. In one embodiment, interference screws can be utilized so that as the interference screws push against the screw holes, the vertebral body bone is compressed against the structure. In addition, the screw cavities 610 can have reverse threads in order to create pressure or resistance for the interference screws. In an additional embodiment, the screws may be placed close enough to the disk space to push against the T arms of the I-beam to compress the cage and improve fixation. In one embodiment, locking pins (e.g., Casper locking pins, or any other locking pins) can be used so that the structure can be locked in place. In one embodiment, there are cut outs 601 for the locking pins at each end of the plate 605, which can be of a shape which corresponds with the shape of the locking pins. Note that the shape of the keel 650 (including the shape of the keel wings 620) can be any shape, as a keel template is made of the keel 650, and the keel template is used to make a keel slot in the structure.

FIG. 6B illustrates a side view of other embodiments of a plate system 690, according to one embodiment of the invention. In this embodiment, a structure 689 is made of two end plates 685 and 684 (which can be of metal or other material) which can vary or alter their angulation after insertion into the spinal column, before placement of the plate 695, and/or before attachment of the plate 695. The structure 689 has an articulating element 688 which can allow adjustment, alteration, or change in angulation of the vertebral bones. When the articulating element 688 is placed so that there is a forward angle (as shown by kyphotic spacer 687), this forward angulation is called kyphosis. When the articulating element is placed so that there is a backward angle (as shown by lordotic spacer 686), this backward anglulation is called lordosis. In this embodiment, the screws 610 attach the plate 695 to the structure 689 and/or the vertebrae. Note that the structure 689 can be used in conjunction with or without the plate described in this or other embodiments.

FIG. 7 illustrates a method 700 for utilizing plate 105 and/or plate 605, according to several embodiments of the invention. In 705, a structure is inserted between two vertebrae. In 710, a keel slot is drilled into the structure, and screw holes are drilled into the vertebrae bones. This allows the keel and the screws to be inserted into the bone. A keel template can be used as a guide for making the keel slot in the structure between the vertebrae. A drill-guide reamer can also be used to drill the screw holes into the vertebrae bones. The holes in the vertebrae bone could be small (e.g., just large enough to allow a small drill to find the middle of the holes). In 715, after the keel template is removed, the plate (with the attached keel) is then inserted into the bone. In 720, the screws are inserted into the screw cavities, and are tightened, attaching the plate firmly to the bone. The screwheads of the screws can be recessed into the vertebrae bone with a drill-guide with a tip, such as a reamer. In one embodiment, the above process can be performed while locking pins (e.g., Casper locking pins, or any other locking pins) are utilized so that the structure can be locked in place. In one embodiment, there are cut outs for the locking pins at each end of the plate, which can be any shape to correspond with the shape of the locking pins. Because the keel and the majority of the screwhead can be inserted into the bone, the plate and the screw heads do not need to stick out substantially from the vertebrae bone.

FIG. 8 illustrates a method of using plate 695, according to one embodiment of the invention. In 805, a structure is inserted between two vertebrae. The structure has two end plates which touch the vertebrae, and an articulating element between the two plates. In 815, the plate is attached to the structure and/or the vertebrae. A keel may or may not be attached to the plate. Screws can be utilized to attach the plate to the structure and/or the vertebrae. Note that throughout this document, something other than a screw may also be used to attach the plates to the structure and/or the vertebrae. In addition, note that any elements of any of the embodiments can be combined to create additional embodiments.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

What is claimed is:

1. A system, comprising:
   a plate having at least one nesting point and at least one screw hole for receiving a screw;
   a keel having a first and second keel wing attached to the plate; and
   a structure comprising at least one screw hole, the structure positionable entirely between adjacent vertebrae in a spine;
   wherein the first and second keel wing are configured with at least one screw hole each which correspond to the at least one screw hole of the plate and the at least one screw hole of the structure,
   wherein the plate and the keel are secured to the structure by attaching the screw through the plate, the keel and the structure to a boney portion of the spine,
   wherein the first and second keel wing are configured with a first and second bottom portion, and the first and second bottom portions having a first and second cup for receiving a portion of the screw and the first and second bottom portions being adapted to lock the screws from backing out.

2. The system of claim 1, wherein the structure contains an articulating element.

3. The system of claim 1, wherein screws are utilized to attach the plate to the structure.

4. The system of claim 1, wherein the angulation of the structure can be altered after the structure enters the human body.

5. The system of claim 1, wherein the structure is a cage, a spacer, a vertebral body replacement, or an intervertebral disk replacement, or any combination of two or more thereof.

6. The system of claim 1, wherein the structure can have end plates which change their angulation relative to each other after insertion within the spine.

7. The system of claim 6, wherein the end plates can change their angulation after placement of the plate and/or before attachment of the plate.

8. The system of claim 1, wherein the structure is a variable angle spacer that can be used in conjunction with or without the plate.

9. The system of claim 1, wherein the plate has holes, the holes allowing screws to be inserted into the plate and screwed into the vertebrae.

10. The system of claim 1, wherein the plate has cups for screw heads of the screws.

11. A system comprising:
- a plate having at least one nesting point and at least one screw hole for receiving a screw;
- a keel having a first and second keel wing attached to the plate; and
- a structure comprising at least one screw hole, the structure positionable entirely between adjacent vertebrae in a spine;
- wherein the first and second keel wing are configured with at least one screw hole each which correspond to the at least one screw hole of the plate and the at least one screw hole of the structure,
- wherein the plate and the keel are secured to the structure by attaching the screw through the plate, the keel and the structure to a boney portion of the spine,
- wherein the at least one nesting point contacts a portion of the structure and the bone portion of the spine
- wherein the first and second keel wing are configured with a first and second bottom portion, and the first and second bottom portions having a first and second cup for receiving a portion of the screw and the first and second bottom portions being adapted to lock the screws from backing out.

* * * * *